United States Patent [19]
Reagen et al.

[11] Patent Number: 5,306,642
[45] Date of Patent: Apr. 26, 1994

[54] DEVICE FOR AQUEOUS DETECTION OF NITRO-AROMATIC COMPOUNDS

[75] Inventors: William K. Reagen, Stillwater, Minn.; Amber L. Schulz, Bremerton, Wash.; Jani C. Ingram, Idaho Falls, Id.; Gregory D. Lancaster, Idaho Falls, Id.; Alan E. Grey, Idaho Falls, Id.

[73] Assignee: The United States of America as represented by the Department of Energy, Washington, D.C.

[21] Appl. No.: 993,552

[22] Filed: Dec. 21, 1992

[51] Int. Cl.⁵ .......................................... G01N 21/64
[52] U.S. Cl. ............................ 436/106; 250/458.1; 250/461.1; 422/82.07; 422/82.08
[58] Field of Search .................. 436/106; 422/58, 63, 422/82.07, 86, 82.08; 250/458.1, 461.1, 461.2; 350/96.29

[56] References Cited

U.S. PATENT DOCUMENTS

| | | | |
|---|---|---|---|
| 3,998,591 | 12/1976 | Eckfeldt | 422/86 |
| 4,108,604 | 8/1978 | Heller | 436/106 |
| 4,650,320 | 3/1987 | Chapman et al. | 250/458.1 |
| 4,737,343 | 4/1988 | Hirschfeld | 422/63 |
| 4,799,756 | 1/1989 | Hirschfeld | 250/458.1 |
| 4,803,049 | 2/1989 | Hirschfeld et al. | 422/58 |
| 4,834,496 | 5/1989 | Blyler, Jr. et al. | 350/96.29 |
| 4,834,497 | 5/1989 | Angel | 350/96.29 |
| 4,861,163 | 8/1989 | Bach | 250/458.1 |
| 4,929,562 | 5/1990 | Anderson et al. | 422/82.07 |
| 5,157,261 | 10/1992 | Grey et al. | 436/106 |
| 5,173,432 | 12/1992 | Lefkowitz et al. | 250/458.1 |

*Primary Examiner*—Robert J. Warden
*Assistant Examiner*—Ramon Torres
*Attorney, Agent, or Firm*—James W. Weinberger; Hugh W. Glenn; William R. Moser

[57] ABSTRACT

This invention relates to a compact and portable detection apparatus for nitro-aromatic based chemical compounds, such as nitrotoluenes, dinitrotoluenes, and trinitrotoluene (TNT). The apparatus is based upon the use of fiber optics using filtered light. The preferred process of the invention relies upon a reflective chemical sensor and optical and electronic components to monitor a decrease in fluorescence when the nitro-aromatic molecules in aqueous solution combine and react with a fluorescent polycyclic aromatic compound.

12 Claims, 4 Drawing Sheets

DEVICE FOR AQUEOUS DETECTION OF NITRO-AROMATIC COMPOUNDS

CONTRACTUAL ORIGIN OF THE INVENTION

The United States Government has rights in this invention pursuant to Contract No. DE-AC07-76ID01570 between the United States Department of Energy and EG&G Idaho, Inc.

FIELD OF THE INVENTION

This invention relates to a compact and portable apparatus and method for detection in water of nitro-aromatic based chemical compounds, such as dinitrotoluene, nitrotoluene and trinitrotoluene (TNT). The portable device can be conveniently carried by an individual, is extremely sensitive to the class of compounds being detected, and is minimally affected by potential interfering substances.

The apparatus of the present invention is based upon the use of fiber optics and a fluorescent compound. A sensor that reflects filtered light emitted from an optical fiber can be constructed that is sensitive, compact, readily portable, and requires a minimum of training for its use. The preferred process of the invention relies upon a chemical system, and optical and electronic components to monitor a decrease in fluorescence when a subject molecule (such as TNT) combines with a fluorescent polycyclic aromatic compound, such as anthracene, phenanthrene, pyrene, or perylene.

Fluorescence occurs when an atom or molecule emits visible radiation when passing from a higher to a lower electronic state. Fluorescent materials may be gas, liquid, or solid, organic, or inorganic. Fluorescent crystals, such as zinc or cadmium sulfide, are used in lamp tubes, television screens, scintillation counters, and similar devices. Fluorescent dyes are used for labeling molecules in biochemical research.

BACKGROUND OF THE INVENTION

The need for detecting nitro-aromatic based chemical compounds, such as nitrotoluene, dinitrotoluene and trinitrotoluene (TNT), is to avoid spread of contamination in ground water that has leached these chemicals in areas where TNT has been disposed of or inadvertently lost.

U.S. Pat. No. 4,108,604 issued to Hiller on Aug. 22, 1968, discloses in a first embodiment, a method for analyzing water for TNT comprising the steps of allowing water to flow over a resin that contains quaternary ammonium groups and is coated with a flourescent dye, and then observing a change in fluorescence of the fluorescent dye. There is no indication of the level of concentration that can be detected by this method and no apparatus is disclosed.

U.S. Pat. No. 5,157,261 filed May 28, 1991 having some common inventors with the instant invention discloses an apparatus for detecting TNT in air. That patent (U.S. Pat. No. 5,157,261) has a common assignee, the United States Department of Energy. The above mentioned application uses a significantly different sensing device. It has a chemically treated fiber optic distal tip for sensing TNT molecules in air which is drawn into the sensor by a vacuum pump.

The present apparatus provides a simple, portable device that detects TNT in water utilizing a simple method and giving accurate results in the parts-per-billion range in a matter of minutes.

SUMMARY OF THE INVENTION

In its simplest form, the portable apparatus consists of a chemically coated plate in a container that is immersed in water. Connecting optical fibers supply filtered light from a broad-band light source and return fluorescent light to a photon sensor which is responsive to a change in light intensity. A suitable electronics assembly activates an alarm when a preset limit (in ppm or ppb) is exceeded.

The mechanism for TNT detection in the chemical sensor is based on fluorescence quenching of a polycyclic aromatic compound trapped in a polymer/solvent matrix and affixed to a glass reflective plate. Excitation of the entrapped compound at selected wavelengths of light energy, i.e., 410 nm, results in strong fluorescence signals at 470 nm. Rapid and measurable quenching of the fluorescence is effected by exposure of the chemical sensor to aqueous solutions of high explosives (TNT).

Testing of the chemical sensor compound has shown rapid and measurable detection of aqueous TNT solutions at 200 ppm, 10 ppm, and 1 ppb levels. Advantages of this sensor over current art include enhanced sensitivity and more rapid in situ detection. These advantages along with the fiber optic design result in a high-explosive sensor amenable to low-cost field application.

The method of detecting parts-per-billion amounts of nitro-aromatic based chemical compounds in water comprises the steps of:

submerging a chemical sensor in the water, the chemical sensor having a supply optical fiber, a return optical fiber, and a chemically coated plate; the plate chemical coating having a combination of perylene (a polycyclic aromatic hydrocarbon), polyethylene (a polymer), and squalane (a high-boiling-point solvent);

activating a filtered light source;

directing a filtered light through fiber optics to a beam splitter;

splitting the filtered light;

directing a first filtered light from the beam splitter through the supply optical fiber to the chemical sensor;

directing a second filtered light from the beam splitter to a reference photon-sensing device;

reflecting the first filtered light from the supply optic fiber to the return optical fiber by means of chemically coated plate;

directing the return optical fiber light to a measurement photon-sensing device;

conducting a reference electrical signal from the reference photon-sensing device to an electronics assembly;

conducting a measurement electrical signal from the measurement photon-sensing device to the electronics assembly;

comparing the measurement electrical signal and the reference electrical signal; and then activating an alarm if the measurement electrical signal decreases below a preset limit as a result of interaction of the explosive chemical compound with the chemically coated plate.

Other objects, advantages, and capabilities of the present invention will become more apparent as the description proceeds.

DETAILED DESCRIPTION OF THE INVENTION

Figure 1:
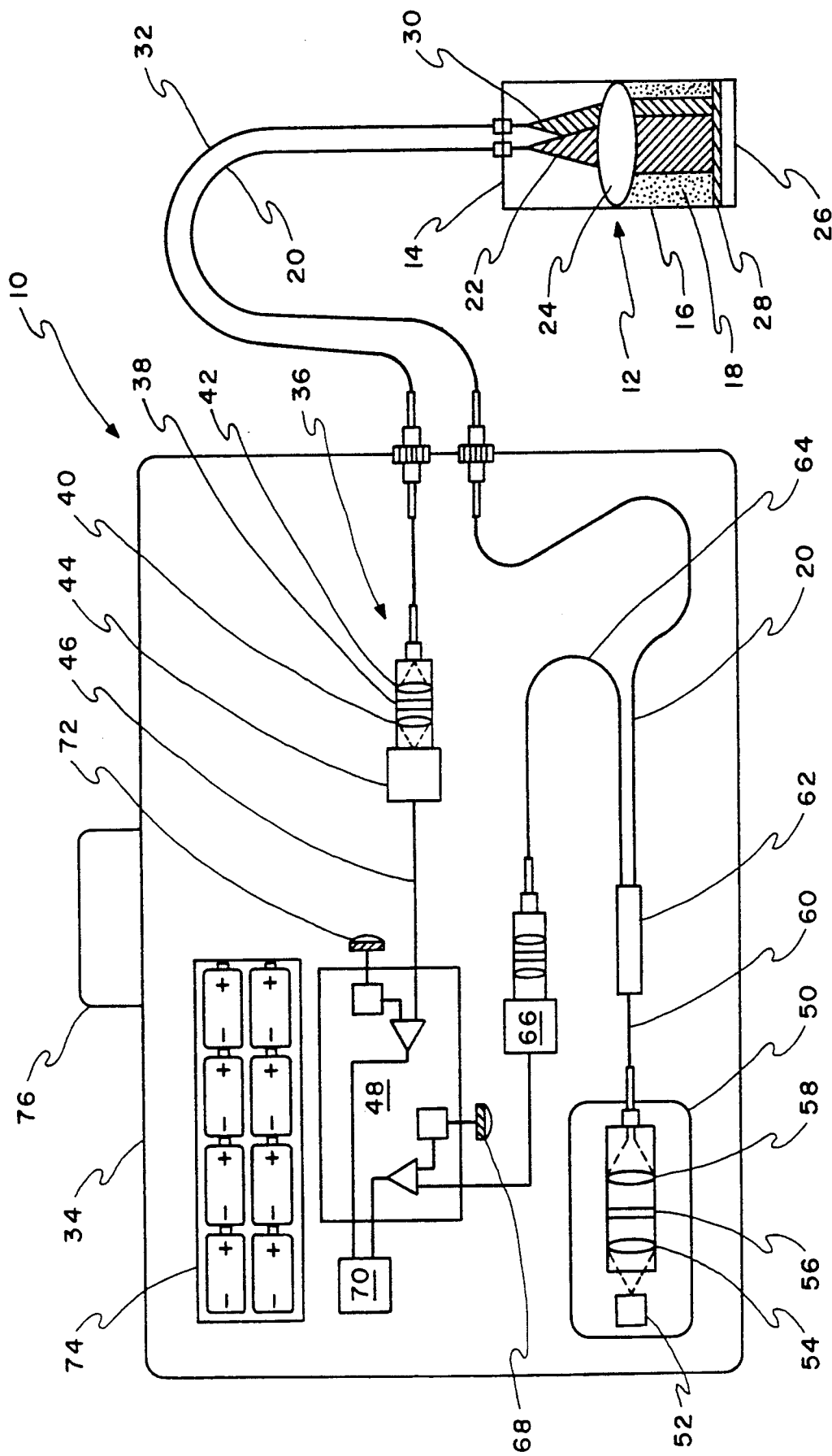
FIG. 1 is a schematic drawing of the present invention.

Referring to FIG. 1, the portable fiber optic detector apparatus for detection of nitro-aromatic based chemical compounds in water is indicated at 10. The chemical sensor 12 consists of a cylinder 14 having a lower perforated section 16 allowing contaminated water 18 within this section 16. A supply optical fiber 20 directs filtered light 22 through a collimating lens 24 and onto plate 26, which has a chemical coating 28 on an inside surface. Fluorescent light 30 from the plate 26 is directed through return optical fiber 32.

This fluorescent light is directed into the carrying case 34 to a measurement photon-sensing device 36 which consists of a 470 nanometer (nm) band pass filter 38 having focusing lenses 40 and 42 on either side to direct the fluorescent light onto a signal detector 44, typically a photodiode. A measurement electrical signal passes through conductor 46 to the electronics assembly 48.

The filtered light source 50 consists of a krypton lamp 52, a focusing lens 54, a 410 nm band pass filter 56, and a second focusing lens 58 which directs the filtered light to fiber optic 60 and then to a beam splitter 62. Beam splitter 62 directs about 95% of the light to the supply optical fiber 20, and about 5% of the filtered light through a reference optical fiber 64 to reference photon-sensing device 66, typically a photodiode having an reference electrical signal proportional to the filtered light intensity. This device 66 compensates for changes in filtered supply light and the electrical signal can be adjusted by potentiometer to change the alarm point after comparison between the reference electrical signal and the measurement electrical signal at 46. Alarm point set potentiometer 68 determines the concentration (parts-per-billion "ppb") at which alarm 70 is activated. Sensitivity to the measurement electrical signal at 46 can be adjusted by sensitivity adjust potentiometer 72. Power is supplied to the lamp 52 and electronics assembly 48 by battery pack 74. The portable case has carrying handle 76.

Figure 2:
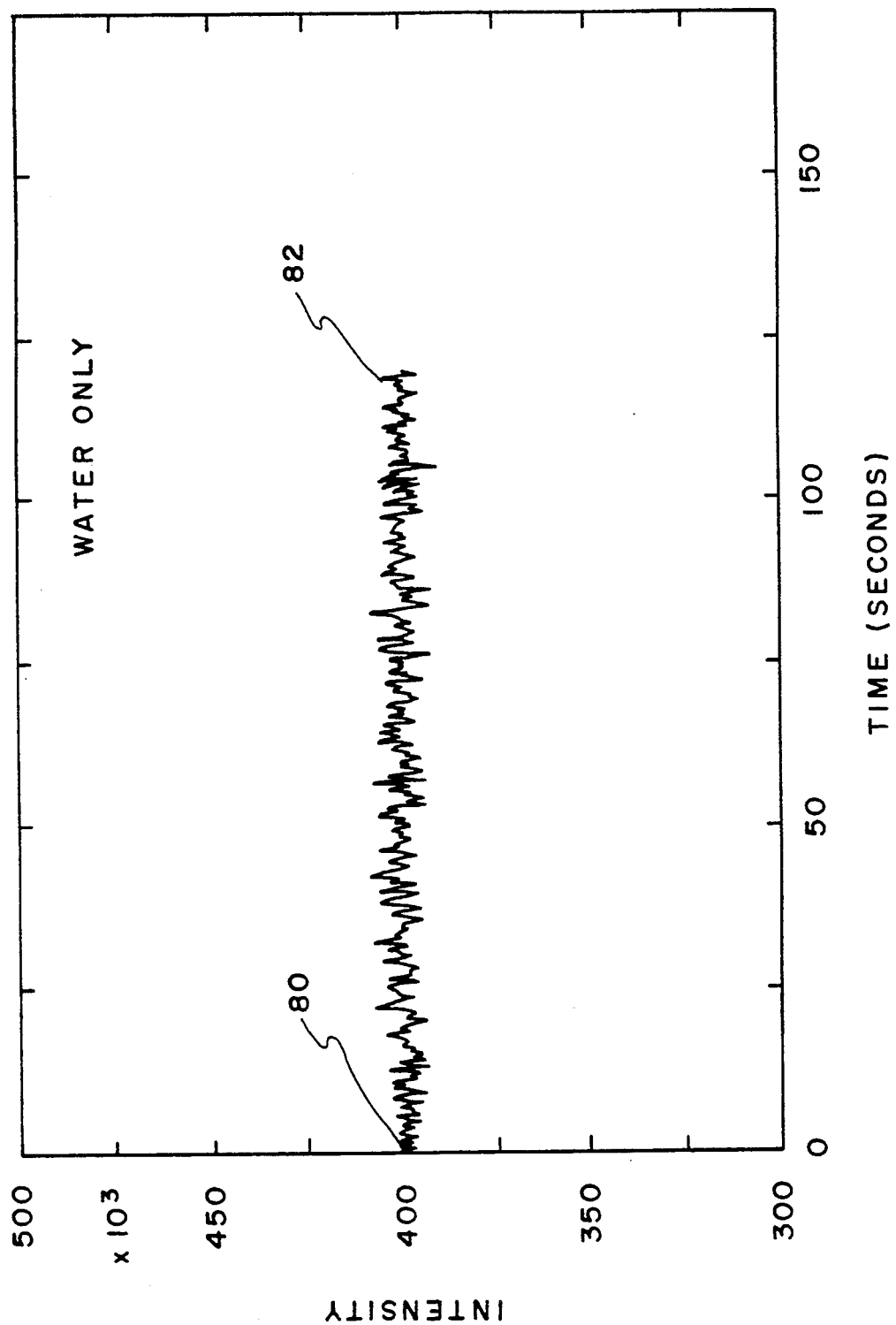
FIG. 2 is a graph of fluorescent light intensity versus time, from the chemical sensor in clean water.
Figure 3:
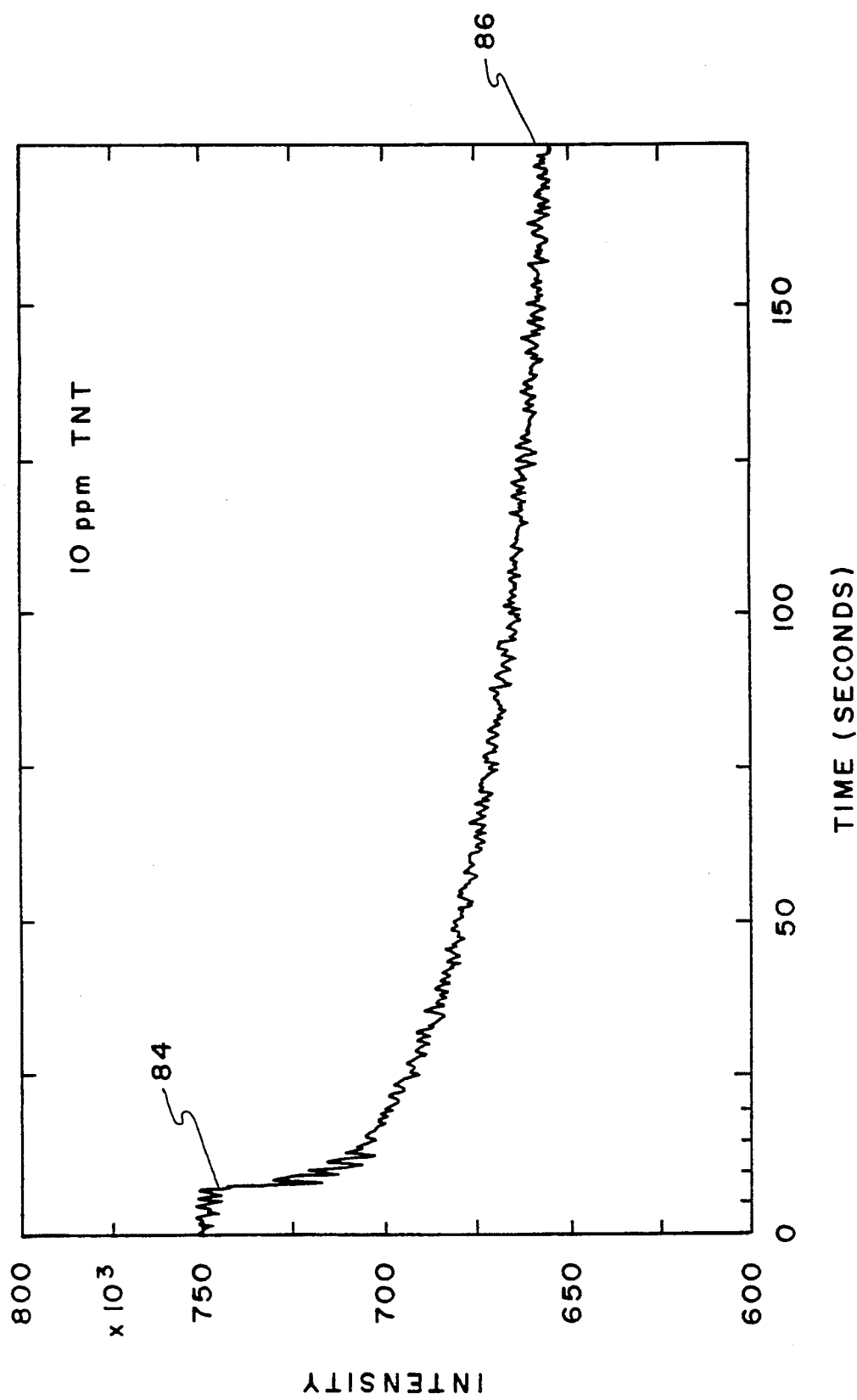
FIG. 3 is a graph of fluorescent light intensity versus time, from the chemical sensor in water having 10 ppm TNT.
Figure 4:
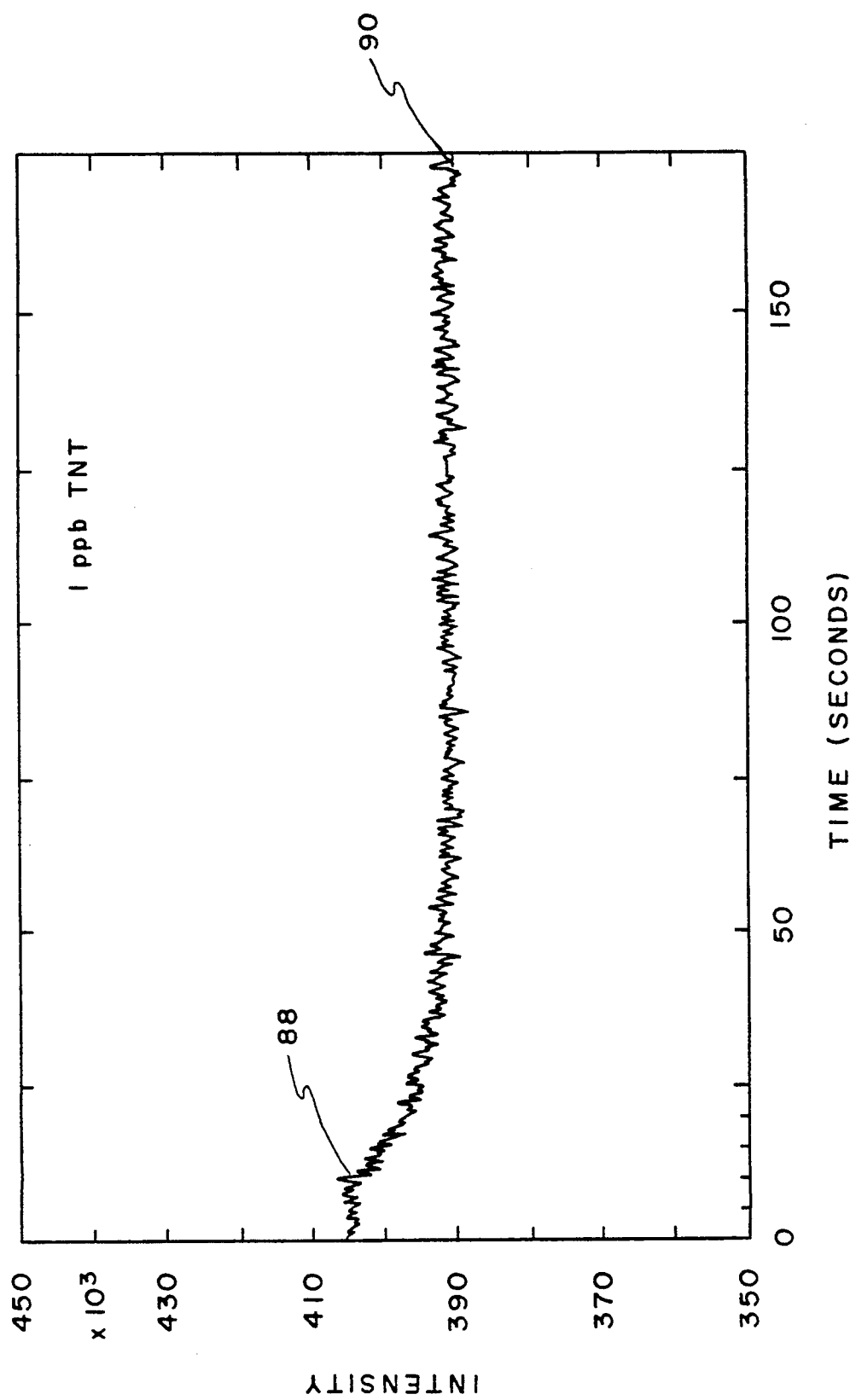
FIG. 4 is a graph of fluorescent light intensity versus time, from the chemical sensor in water having 1 ppb TNT.

The results of experimental data using a chemical coating on the sensor consisting of perylene, polyethylene, and squalane, are illustrated in the graphs of FIGS. 2, 3, and 4. FIG. 2 is a control experiment where the probe is immersed in clean water. The curve remains flat from beginning intensity 80 to end 82 after about 150 seconds indicating a lack of quenching at the chemically coated surface in contact with the water. The intensity is in arbitrary units, which are proportional to luminosity.

Experimental tests have been performed at 200 ppm, which approaches the limit of solubility of 1000 ppm TNT in water as defined by the Merck index of solubility: 0.01% at 25° C. This test data indicated quenching and light intensity reduction but is not presented here. The data would produce a curve similar to FIG. 3.

FIG. 3 demonstrates the intensity reduction occurring after immersing the sensor in 10 ppm TNT in water. At about 5 seconds, the sensor is immersed and the intensity drops from $750 \times 10^3$ at 84° C. to about $655 \times 10^3$ at 86° C. after 175 seconds, representing about 12% reduction from the initial intensity.

FIG. 4 demonstrates sensing a solution of 1 ppb of TNT in water. Immersion at about 10 seconds shows an intensity drop from about $405 \times 10^3$ at 88° C. to about $390 \times 10^3$ at 90° C. after 175 seconds. This represents about a 4% reduction even at this very low concentration.

Other tests have identified an optimized procedure for preparing the plate chemical coating. The preferred method being to spin-coat the liquid on the plate and then age the coating in air to allow an absorption process to adhere the liquid to the plate. Aging for six weeks provides a tenacious coating that remains on the plate for repeated immersions in water. Without aging, the applied liquid tends to wash off the plate.

The liquid coating preferred mixture is prepared by heating 150 mg of 0.915 density polyethylene with 10 ml of squalane until the polyethylene is melted. Remove the heat and allow the liquid to cool for about one minute and then add by stirring in 5 mg of perylene, the fluorescing compound.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

What is claimed is:

1. A portable fiber optic detector apparatus for detecting dissolved nitro-aromatic based chemical compounds in water comprising:
   a. a chemical sensor further comprising:
      i. a cylinder having a lower perforated section thereby allowing water entry;
      ii. a chemical coating on a glass plate within the lower perforated section of the cylinder;
      iii. a focusing lens within the cylinder above the glass plate;
      iv. a supply and a return optical fiber having a first end penetrating an upper section of the cylinder above the focusing lens;
   b. a case containing a battery, an electronics assembly, and an alarm;
   c. a measurement photon-sensing device connected to the electronics assembly having an input from a second end of the return optical fiber and an output to the electronics assembly;
   d. a filtered light source optically connected to a beam splitter input, said beam splitter having a fiber optic output to a reference photon-sensing device and the supply fiber; and
   e. a reference photon-sensing device output connected to the electronics assembly; and wherein the dissolved chemical compounds in the water cause a reduction in fluorescent intensity at the chemically coated glass plate whereby a fluorescent light is directed through the water and return optic fiber, said reduction can be detected by the measurement photon-sensing device and the alarm can be activated.

2. The apparatus as recited in claim 1 wherein the measurement photon-sensing device further comprises a photodiode, a pair of focusing lenses, and a 470 nm band pass filter.

3. The apparatus as recited in claim 2 wherein the filtered light source further comprises a krypton light, a pair of focusing lenses, and a 410 nm band pass filter.

4. The apparatus as recited in claim 3 wherein the plate coating further comprises a mixture of perylene, squalane, and polyethylene that has been aged in air for a period of about six weeks.

5. A fiber optic detector apparatus for detecting dissolved nitro-aromatic based chemical compounds in concentrations as low as 1 ppb in water comprising:
   a. a chemical sensor further comprising:
      i. a cylinder having a lower perforated section thereby allowing water entry;
      ii. a chemical coating on a plate within the lower perforated section of the cylinder wherein the plate coating further comprises a mixture of perylene, squalane, and polyethylene that has been aged in air for a period of six weeks;
      iii. a focusing lens within the cylinder above the plate;
      iv. a supply and a return optical fiber having a first end penetrating an upper section of the cylinder above the focusing lens;
   b. a case containing a battery, an electronics assembly, and an alarm;
   c. a measurement photon-sensing device connected to the electronics assembly having an input from a second end of the return optical fiber and an output to the electronics assembly;
   d. a filtered light source optically connected to a beam splitter input, said beam splitter having a fiber optic output to a reference photon-sensing device and the supply fiber; wherein a reference photon-sensing device output to the electronics assembly compensates the assembly output for changes in light intensity, and a reduction in fluorescent intensity from the dissolved chemical compounds in the water at the chemically coated plate and return optic fiber can be detected by the measurement photon-sensing device and the alarm can be activated.

6. The apparatus as recited in claim 5 wherein the plate coating further comprises a heated and then cooled mixture of squalane and polyethylene to which perylene is added.

7. The apparatus as recited in claim 6 wherein the measurement photon-sensing device further comprises a photodiode, a pair of focusing lenses, and a 470 nm band pass filter.

8. The apparatus as recited in claim 7 wherein the filtered light source further comprises a krypton light, a pair of focusing lenses, and a 410 nm band pass filter.

9. A method of detecting parts-per-billion amounts of dissolved nitro-aromatic based chemical compounds in water comprising the steps of:
   a. submerging a chemical sensor in the water permitting water to enter a lower section of the chemical sensor, said chemical sensor having a supply optical fiber, a return optical fiber, and a chemically coated plate; said plate coating having a combination of perylene, polyethylene, and squalane;
   b. activating a filtered light source;
   c. directing a filtered light though fiber optics to a beam splitter;
   d. splitting the filtered light;
   e. directing a first filtered light from the beam splitter through the supply optical fiber to the chemical sensor;
   f. directing a second filtered light from the beam splitter to a reference detector;
   g. reflecting the first filtered light from the supply optical fiber through the water to the return optical fiber, at a reduced light intensity, by means of the chemically coated plate;
   h. directing the return optical fiber light to a photon-sensing device;
   i. conducting a reference electrical signal from the reference detector to an electronics assembly;
   j. conducting a photon-sensing device electrical signal &rom the photon-sensing device to the electronics assembly;
   k. comparing the photon-sensing device electrical signal and the reference electrical signal; and then
   l. activating an alarm if the photon-sensing device electrical signal decreases below a present limit as a result of interaction of the dissolved chemical compound with the chemical coated plate.

10. The method as recited in claim 9 wherein the photon-sensing device further comprises a photodiode, a pair of focusing lenses, and a 470 nm band pass filter.

11. The method as recited in claim 10 wherein the filtered light source further comprises a krypton light, a pair of focusing lenses, and a 410 nm band pass filter.

12. The method as recited in claim 11 wherein the plate coating &urther comprises a heated and then cooled mixture of squalane and polyethylene to which perylene is added.

* * * * *